United States Patent [19]

Thirumalachar et al.

[11] 4,218,445

[45] Aug. 19, 1980

[54] N,N'DIBENZYLETHYLENEDIAMINE-DIACETYLSALICYLATE, A NOVEL CHEMOTHERAPEUTIC AGENT FOR PAIN RELIEF BY EXTERNAL APPLICATION

[76] Inventors: Mandayam J. Thirumalachar, 514 Huron St. SE., Apt. 1; Mandayam J. Narasimhan, Jr.; Mandayam J. Kasthuri-Thirumalachar, both of 514 Huron St. SE., all of Minneapolis, Minn. 55414

[21] Appl. No.: 904,008

[22] Filed: May 8, 1978

[51] Int. Cl.² ..................... A61K 31/60; A61K 31/61; A61K 31/625

[52] U.S. Cl. ................................. 424/230; 424/232; 424/234; 560/143

[58] Field of Search ....................... 424/230, 232, 234; 260/501.2; 560/143

[56] References Cited

U.S. PATENT DOCUMENTS

| 2,627,491 | 2/1953 | Szabr et al. | 260/501.2 |
| 2,748,139 | 5/1956 | Scudi et al. | 260/501.2 |
| 3,629,333 | 12/1971 | Boughton et al. | 260/501.2 |

*Primary Examiner*—Stanley J. Friedman
*Attorney, Agent, or Firm*—Warren A. Sturm

[57] ABSTRACT

N, N'-dibenzylethylenediamine-diacetylsalicylate for effecting an analgesic, antipyretic, spasmolytic or anti-inflammatory response in a mammalian host.

12 Claims, No Drawings

N,N'DIBENZYLETHYLENEDIAMINE-DIACETYL-SALICYLATE, A NOVEL CHEMOTHERAPEUTIC AGENT FOR PAIN RELIEF BY EXTERNAL APPLICATION

BACKGROUND OF THE INVENTION

In the long search for effective medicaments to alleviate pain of different types, no other group of drugs have dominated the field more than the salicylates, which by virtue of their analgesic, antipyretic and antirheumatoid properties have been the drug of choice. The salicylates have many modes of action, some of which are not well understood, but they all have selective depressent effect on the central nervous system. While salicylic acid is very irritating and can be used only externally, the esters produced by the substitution of the hydroxyl group are extremely useful in oral therapy, such as acetylsalicylic acid or aspirin. When the carboxyl group is substituted, as in sodium salicylate or methylsalicylate, the irritant effect in the compound is still present.

In a recent U.S. Patent application (Ser. No. 841,734) the petitioners presented a novel chemical derivative of acetylsalicylic acid or aspirin, by the production synthetically N-N'dibenzylethylenediamine-diacetylsalicylate or DBED-aspirin which had lesser toxicity than aspirin or salicylamide (LD-50 by oral route in mice for DBED-aspirin is 3.5 grams/kg as against 1.75 grams/kg for aspirin and 1.4 grams/kg for salicylamide). It was also briefly mentioned that the DBED-aspirin when applied externally as an ointment was subcutaneously absorbed and brought about immediate pain relief. This obviated the oral administration salicylates. It further had the advantage of being used as a combined fortified therapy along with other pain killing agents.

Though considered safe, acetylsalicylic acid has its own adverse effects in some patients. Epigastric disturbances as vomitting, nausea often accompany oral treatment. Other forms of salicylate poisoning are well documented in medical literature. It is in this context that DBED-aspirin, a safe, non-irritant and highly potent analgesic substance is presented, which by its property of subcutaneous absorption when applied externally on skin, has a unique place in treatment of pain.

DBED-salts of penicillin, such as benzathine penicillin are used as injectables and by their depot action they give long sustained blood levels. The DBED-penicillin slowly breaks up into DBED molecule and penicillin. Thus it is seen that DBED molecule in blood stream is fairly non-toxic and well tolerated. However, the finding that in combination with acetylsalicylic acid and DBED molecule, a subcutaneously absorbed chemotherapeutant is produced, is a novel finding in the present invention.

PRECLINICAL STUDIES IN ANIMALS

Since DBED-aspirin is being recommended for external application, a 20% preparation was made in an ointment base and applied on the ear of rabbit daily for 90 days. There were no adverse effects of any kind. In another set of experiments, the rabbit's ears were scarified with a sharp point to the point of reddening and slight bleeding, and 5% DBED-aspirin ointment was applied on this scarified surface, once daily for 2 days. There was immediate response in lessening of the inflammation within 10 hours after the first application and healing after 8 hours of the second application.

CLINICAL STUDIES IN HUMANS

All the studies on humans for treatment against pain by external application were made in countries outside the United States and the effective analgesic and antirheumatoid properties of DBED-aspirin was established. The persons treated were under expert medical supervision, where the effects of treatments were compared with scheduled drugs in current use as well as placebo. The following examples illustrate the effect of DBED-aspirin ointment in the treatment of pain.

EXAMPLE 1

100 cases of severe headache of the migrane type and 120 cases of muscular pain of the shoulders and nape of the neck, similar to the "executive shoulders" were chosen. Half the number in each group were treated with well known remedies currently used, and the other half with 5% DBED-aspirin ointment. Another set of the same number were given orally placebo tablets. In case of headache DBED-aspirin (5%) ointment was applied externally at the site of pain. The positive control groups were given 2 APC tablets (aspirin-phenacetin-caffein) orally twice at intervals of 6 hours. The placebo given orally contained calcium carbonate only. In all the treated cases with DBED-aspirin ointment, there was immediate relief of pain 12 to 15 minutes after application, the patients being able to concentrate on their work again and feeling refreshed. In case of APC tablets, 35 patients felt relieved 15 minutes after the first treatment and the rest got relief after both the doses. The placebo was ineffective in all cases.

EXAMPLE 2

60 Patients in a dental clinic were taken with cases of tooth extraction for caries, 35 of which were cases involving molar teeth. 60 Similar cases were taken for the usual treatment of giving high doses of commercially available pain-killer Novalgin. 60 Other cases were set apart for placebo. In all these cases the patients were of all age groups, and only those cases which could be followed up were taken. This study took more than two years for completion.

In case of DBED-aspirin ointment treatment of 5% concentration, the patients immediately after the extraction of tooth or teeth, as the case may be, were asked to apply the ointment externally on the jaw or cheek corresponding to the position of the tooth taken out. This was external on the outer skin and not the gum. They were asked to apply twice or thrice within the next 24 hours before they reported back to the clinic. In case of Novalgin treatment, the patient was given 3 tablets, one immediately after tooth extraction and two others for the ensuing period of 24 hours. In case of placebo, calcium carbonate tablets looking similar to Novalgin were given.

Observations were carefully recorded. In all cases of DBED-aspirin ointment treatment, immediately after the after-effects of xylocane, which had kept the pain of tooth extraction down by benumbing effect, was gone, the patient felt no pain and was able to sleep during the night normally. The patients felt extremely well when they reported to the clinic next day. In case of Novalgin, the patients felt throbbing pain after 3 hours, which was only partly relieved after the administration of two more doses. The pain was manageable but not the complete comfort as in DBED-aspirin ointment. In case of the placebo, particularly after the molar tooth extraction, the pain became so intense that had to be treated with heavy sedation and external application of Sloan's linament (capsicin) and Algipen (histamine containign) which by their counter-irritation effect gave tolerable relief.

There was no irritation, reddening or hyperaemia of the skin with the application of DBED-aspirin ointment. In case of analgesics used externally, such as methyl salicylate, capsicin, histamines etc., the main principle is counter-irritation. In discussing salicylate analgesia, Robert K. Lim (in the "Salicylates" ed. Smith and Smith, Interscience Publishers 1966), states that "less unanimity prevails with regard to their efficacy (salicylates) in such conditions such as toothache . . . ". In this regard DBED-aspirin has proved to be an exception in being effective in relieving tooth-ache pain.

EXAMPLE 3

Besides analgesia, there is spasmolytic type of effect in muscular pains, especially in the weight bearing extremities. The following 150 cases are those who had muscular pain of different types, many of which were of long duration and had been treated with various available analgesic agents, internal as well as external, including radiation therapy without much relief.

(3-A).

30 Cases of trauma with intense swelling and pain due to being hit by ball in cricket or tennis were treated. DBED-aspirin 5% ointment was applied at the site, and within 2 hours hyperaemia disappeared and the patient felt no discomfort or pain. 10 other persons with similar cases were treated with the commercially available analgesics, and the reddening and burning became so intense after application of these external analgesics due to their irritant action, that the patient had to be treated with corticosteroids and other treatments.

(3-B)

20 Persons who had developed muscular pain at the ankle and could not wear the shoes, since the pain became aggravated (8 among them were medical personnel who had taken all known remedies including cortcosteroids). DBED-aspirin ointment (5%) was applied twice daily. From 5th.day onwards there was no pain and all of them were able to wear shoes again.

(3-C)

50 Cases were taken in an orthopediac clinic, where cases with trauma due to accidents, osteoarthritis, chronic arthritis, big toe etc. were being treated with drugs in current therapy. All these cases when treated with DBED-aspirin (5%) ointment, responded excellently and according to the orthopediatrician, DBED-aspirin ointment has given the most beneficial effect in the treatment of such cases.

(3-D)

20 Cases of arthritis where the patients felt pain and extreme rigidity, were treated with DBED-spirin ointment (5%) in the orthopediac clinic. 15 minutes after the application of the ointment, the patients felt lessening of pain, and were able to move freely for 8 to 10 hours. During this period they felt more comfortable than at any other time with other treatments such as oral phenylbutazone.

(3-E)

20 Cases of myosotis and muscular pain accompanying influenza type of affections of the upper respiratory tract, which during the spreading stages of infenction are known to have transient viremia, the muscular pain being attributed to viral myosotis by some medical doctors, application of 5% DBED-aspirin ointment gave remarkable relief from body pain, muscular pain, which is one of the main causes of discomfort. There is at present no other medicament for this except complete rest.

It may be concluded that by its subcutaneous absorption by external application at the site of pain, DBED-aspirin ointment is able to give relief in cases mentioned above, such as spasms, twitches of muscles, contractile pyotendinous elements, fibro and teno-myosotis, relief from rheumatoid type of joint pains and the like. Topical application has shown marked relief of pain, swelling and other classical inflammatory signs of arthritis, bursitis and teno-synovitis. Its immense curative and relief effects in cases of pains due to tooth extraction has proved its extreme efficacy and usefulness. Its low toxicity and long shelf-life both as pure material and as formulations, warrants its place among potent drugs for treatment of pain.

The analgesic effect of salicylates is not due to the liberation of salicylic acid by hydrolysis, but due to the whole molecule itself. This was shown by Lester, Lolli and Greenberg (J. Pharmacol. 87:329–342, 1946). For instance, the total salicylate concentration in plasma required to block pain receptors with aspirin is 3.1 mg/per 100 cc, as compared with 16.1 mg/per 100 cc of plasma in case of sodium salicylate. DBED-molecule is non-toxic as indicated by its use in the injectable DBED-penicillin, also known as benzathine penicillin.

We claim:

1. A method of effecting an analgesic, antipyretic, spasmolytic or antiinflammatory response in a mammalian host comprising administering to the host a response-effective amount of N,N'-dibenzylethylenediamine-diacetylsalicylate.

2. A method according to claim 1, wherein the N,N'-dibenzylethylenediamine-diacetylsalicylate is administered topically.

3. A method according to claim 2, wherein the host is human.

4. A method according to claim 3, wherein the N,N'-dibenzylethylenediamine-diacetylsalicylate is administered in combination with an excipient.

5. A method according to claim 4, wherein the N,N'-dibenzylethylenediamine-diacetylsalicylate is administered in ointment, cream, lotion or dusting powder form.

6. A method according to claim 1, wherein the N,N'-dibenzylethylenediamine-diacetylsalicylate is administered orally.

7. A method according to claim 6, wherein the host is human.

8. A method according to claim 7, further comprising the combined fortified therapeutic administration of an analgesic.

9. A method according to claim 7, wherein the N,N'-dibenzylethylenediamine-diacetylsalicylate is administered in combination with an excipient.

10. A chemotherapeutic composition for topical application having analgesic, antipyretic or antirheumatoidal properties comprising a topically-applied effective amount of N,N'-dibenzylethylenediamine-diacetylsalicylate and an excipient.

11. A chemotherapeutic composition according to claim 10, wherein the excipient is in the form of an ointment, cream, lotion or dusting-powder formulation amount.

12. A chemotherapeutic ointment composition for topical application having analgesic, antipyretic or antirheumatoid properties consisting essentially of N,N'-dibenzylethylenediamine-diacetylsalicylate and an ointment-forming excipient.

* * * * *